United States Patent
Funk et al.

(10) Patent No.: US 7,144,957 B2
(45) Date of Patent: Dec. 5, 2006

(54) POLYMER MIXTURE OF HYDROGELS WITH DIFFERENT PH VALUE

(75) Inventors: Rüdiger Funk, Niedernhausen (DE); Norbert Herfert, Charlotte, NC (US); Mariola Wanior, Erlensee (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 296 days.

(21) Appl. No.: 10/490,403

(22) PCT Filed: Sep. 26, 2002

(86) PCT No.: PCT/EP02/10793

§ 371 (c)(1),
(2), (4) Date: Mar. 23, 2004

(87) PCT Pub. No.: WO03/028778

PCT Pub. Date: Apr. 10, 2003

(65) Prior Publication Data

US 2004/0249079 A1  Dec. 9, 2004

(51) Int. Cl.
*C08L 33/02* (2006.01)
(52) U.S. Cl. ...... 525/178; 525/179; 525/218; 525/221; 525/227; 524/522; 524/916

(58) Field of Classification Search ......... 525/178, 525/179, 218, 221, 227; 524/522, 916
See application file for complete search history.

(56) References Cited

U.S. PATENT DOCUMENTS

| 5,145,906 A | 9/1992 | Chambers et al. |
| 6,258,996 B1 * | 7/2001 | Goldman ............ 604/368 |

FOREIGN PATENT DOCUMENTS

| DE | 195 29 348 | 2/1997 |
| EP | 0 205 674 | 12/1986 |
| EP | 0 349 240 | 1/1990 |
| EP | 0 467 073 | 1/1992 |
| EP | 0 530 438 | 3/1993 |
| WO | WO 99/25393 | 5/1999 |
| WO | WO 01/32117 | 5/2001 |
| WO | WO 01/32226 | 5/2001 |

* cited by examiner

Primary Examiner—James J. Seidleck
Assistant Examiner—Olga Asinovsky
(74) Attorney, Agent, or Firm—Marshall Gerstein & Borun LLP

(57) ABSTRACT

The present invention relates to polymer mixtures comprising hydrogel forming polymers capable of absorbing aqueous fluids, having different pH values and each being preparable by polymerization of olefinically unsaturated carboxylic acids or derivatives thereof, their preparation, use and hygiene articles containing same. More particularly, the invention relates to 2-component polymer mixtures comprising polymers having a pH range from acidic to neutral.

11 Claims, No Drawings

POLYMER MIXTURE OF HYDROGELS WITH DIFFERENT PH VALUE

CROSS-REFERENCE TO RELATED APPLICATION

This is the U.S. national phase application of International Application No. PCT/EP02/10793, filed Sep. 26, 2002.

The present invention relates to polymer mixtures comprising hydrogel forming polymers capable of absorbing aqueous fluids, having different pH values and each being preparable by polymerization of olefinically unsaturated carboxylic acids or derivatives thereof, their preparation, use and hygiene articles containing same. More particularly, the invention relates to 2-component polymer mixtures comprising polymers having a pH range from acidic to neutral.

Swellable hydrogel forming addition polymers, known as superabsorbent polymers or SAPs, are known from the prior art. They are networks of flexible hydrophilic addition polymers, which can be both ionic and nonionic in nature. They are capable of absorbing and binding aqueous fluids by forming a hydrogel and therefore are preferentially used for manufacturing tampons, diapers, sanitary napkins, incontinence articles, training pants for children, insoles and other hygiene articles for the absorption of body fluids. Superabsorbents are also used in other fields of technology where fluids, especially water or aqueous solutions, are absorbed. These fields include for example storage, packaging, transportation (packaging material for water-sensitive articles, for example flower transportation, shock protection); food sector (transportation of fish, fresh meat; absorption of water, blood in fresh fish/meat packs); medicine (wound plasters, water-absorbent material for burn dressings or for other weeping wounds); cosmetics (carrier material for pharmaceuticals and medicaments, rheumatic plasters, ultrasound gel, cooling gel, cosmetic thickeners, sunscreen); thickeners for oil/water or water/oil emulsions; textiles (gloves, sportswear, moisture regulation in textiles, shoe inserts); chemical process industry applications (catalyst for organic reactions, immobilization of large functional molecules (enzymes), adhesive for agglomerations, heat storage media, filtration aids, hydrophilic component in polymer laminates, dispersants, liquefiers); building construction, installation (powder injection molding, clay-based renders, vibration-inhibiting medium, assistants in relation to tunneling in water-rich ground, cable sheathing); water treatment, waste treatment, water removal (de-icers, reusable sandbags); cleaning; agriculture industry (irrigation, retention of meltwater and dew precipitates, composting additive, protection of forests against fungal and insect infestation, delayed release of active ingredients to plants); fire protection (flying sparks)(covering houses or house walls with SAP gel, since water has a very high heat capacity, ignition can be prevented; spraying of SAP gel in the case of fires such as for example forest fires); coextrusion agent in thermoplastic polymers (hydrophilicization of multilayer, films; production of films and thermoplastic moldings capable of absorbing water (for example agricultural films capable of storing rain and dew water; SAP-containing films for keeping fresh fruit and vegetables which can be packed in moist films; the SAP stores water released by the fruit and vegetables without forming condensation droplets and partly reemits the water to the fruit and vegetables, so that neither fouling nor wilting occurs; SAP-polystyrene coextrudates for example for food packs such as meat, fish, poultry, fruit and vegetables); carrier substance in active-ingredient formulations (drugs, crop protection). Within hygiene articles, superabsorbents are generally positioned in an absorbent core which, as well as SAP, comprises other materials, including fibers (cellulose fibers), which act as a kind of liquid buffer to intermediately store the spontaneously applied liquid insults and are intended to ensure efficient channelization of the body fluids in the absorbent core toward the superabsorbent.

The current trend in diaper design is toward ever thinner constructions having a reduced cellulose fiber content and an increased hydrogel content. The trend toward ever thinner diaper constructions has substantially changed the performance profile required of the water swellable hydrophilic polymers over the years. Whereas at the start of the development of highly absorbent hydrogels it was initially solely the very high swellability on which interest focused, it was subsequently determined that the ability of the superabsorbent to transmit and distribute fluid is also of decisive importance. It has been determined that conventional superabsorbents greatly swell at the surface on wetting with liquid, so that transportation of liquid into the particle interior is substantially compromised or completely prevented. This trait of superabsorbents is known as gel blocking. The greater amount of polymer per unit area in the hygiene article must not cause the swollen polymer to form a barrier layer to subsequent fluid. A product having good transportation properties will ensure optimal utilization of the entire hygiene article. This prevents the phenomenon of gel blocking, which in the extreme case will cause the hygiene article to leak. Fluid transmission and distribution is thus of decisive importance with regard to the initial absorption of body fluids.

Good transportation properties are possessed for example by hydrogels having high gel strength in the swollen state. Gels lacking in strength are deformable under an applied pressure (pressure due to bodyweight) and clog the pores in the SAP/cellulose fiber absorbent and so prevent continued absorption of fluid. Enhanced gel strength is generally obtained through a higher degree of crosslinking, although this reduces retention performance. An elegant way to enhance gel strength is surface postcrosslinking. In this process, dried superabsorbents having an average crosslink density are subjected to an additional crosslinking step. The process is known to one skilled in the art and described in EP-A-0 349 240. Surface postcrosslinking increases the crosslink density in the sheath of the superabsorbent particle, whereby the absorbency under load is raised to a higher level. Whereas the absorption capacity decreases in the superabsorbent particle sheath, the core has an improved absorption capacity (compared to the sheath) owing to the presence of mobile polymer chains, so that sheath construction ensures improved fluid transmission without occurrence of the gel blocking effect. It is perfectly desirable for the total capacity of the superabsorbent to be occupied not spontaneously but with time delay. Since the hygiene article is generally repeatedly insulted with urine, the absorption capacity of the superabsorbent should sensibly not be exhausted after the first disposition.

When hydrogels are used in the hygiene sector, they become exposed to body fluids such as urine or menses. Body fluids generally contain malodorous components of the amine or fatty acid type, which appear alongside the organic components anyhow present, for example, amines, acids, alcohols, aldehydes, ketones, phenols, polycyclics, indoles, aromatics, polyaromatics, etc., that are responsible for unpleasant body odors. Odor development takes place in two stages, first in the course of exudation from the body region and then when the fluid has already been present in the absorption medium for a defined time. Both odor factors have to be eliminated, since it is undesirable for cost reasons to change the hygiene article after every absorption process.

The literature on odor control in the hygiene sector reveals the following approaches:

Odor control coupled with simultaneous absorption by addition of inert inorganic substances having a large surface area, generally as a solid onto the surface of powders or granules for manufacturing absorbent polymers. Zeolites, active carbon, bentonites, finely divided amorphous silicas such as AEROSIL® or CAB-O-SIL® are used here.

Addition of substances capable of complexing with organic molecules or with metal ions present in the body fluid to prevent the development of unpleasant odors. This preferably takes the form of the use of cyclodextrins (any modification of unsubstituted cyclodextrins which contains from 6 to 12 glucose units, for example alpha-cyclodextrin, beta-cyclodextrin, gamma-cyclodextrin and/or derivatives and/or mixtures thereof). Mixtures of cyclodextrins are preferred, since they provide broader complexation of organic molecules over a wider molecular weight range. Cyclodextrins are used in amounts from 0.1% to about 25%, preferably from 1% to about 20%, more preferably from 2% to about 15% and especially from 3 to 10%, based on the total weight of the composition. Cyclodextrins are added in small particle size (usually less than 12 μm) to offer a large surface area for odor elimination. Further complexing agents are aminopolycarboxylic acids and their salts, ethylenediaminetetraacetate EDTA ethylenediaminepentamethylenephosphonic acid, ethylenediaminetetramethylenephosphonic acid, aminophosphates, polyfunctional aromatics, N,N-disuccinic acid.

Masking of unpleasant odors by addition of perfumes or deodorants. These are added in free form or in encapsulated form (for example in cyclodextrins). The latter form makes it possible to release the perfume with a time delay. Nonlimiting examples of perfumes are allyl caproate, allylcyclohexane acetate, allylcyclohexane propionate, allyl heptanoate, amyl acetate, amyl propionate, anetole, anisole, benzaldehyde, benzyl acetate, benzylacetone, benzyl alcohol, benzyl butyrate, benzyl formate, benzyl isovalerate, benzyl propionate, butyl benzoate, butyl caproate, camphor, cis-3-hexenyl acetate, cis-3-hexenyl butyrate, cis-3-hexenyl caproate, cis-3-hexenyl valerate, citronellol, citronellyl derivatives, Cyclal C, cyclohexylethyl acetate, 2-decenal, decylaldehyde, dihydromyrcenol, dimethylbenzylcarbinol and derivatives thereof, dimethyloctanol, diphenyl oxide, ethyl acetate, ethyl acetoacetate, ethyl amyl ketone, ethyl benzoate, ethyl butyrate, ethyl hexyl ketone, ethyl phenylacetate, eucalyptol, fenchyl acetate, fenchyl alcohol, tricyclodecenyl acetate, tricyclodecenyl propionate, geraniol, geranyl derivatives, heptyl acetate, heptyl isobutyrate, heptyl propionate, hexenol, hexenyl acetate, hexenyl isobutyrate, hexyl acetate, hexyl formate, hexyl isobutyrate, hexyl isovalerate, hexyl neopentanoate, hydroxycitronellal, α-ionone, β-ionone, γ-ionone, isoamyl alcohol, isobornyl acetate, isobornyl propionate, isobutyl benzoate, isobutyl caproate, isononyl acetate, isononyl alcohol, isomenthol, isomenthone, isononyl acetate, isopulegol, isopulegyl acetate, isoquinoline, dodecanal, lavandulyl acetate, ligustral, δ-limonene, linalool and derivatives, menthone, menthyl acetate, methylacetophenone, methyl amyl ketone, methyl anthranilate, methyl benzoate, methyl benzylacetate, methylchavicol, methyleugenol, methylheptenone, methyl heptynecarbonate, methyl heptyl ketone, methyl hexyl ketone, methylnonylacetaldehyde, α-iso"γ"methylionone, methyloctylacetaldehyde, methyl octyl ketone, methylphenylcarbinyl acetate, methyl salicylate, myrcene, myrcenyl acetate, neral, nerol, neryl acetate, nonalactone, nonyl butyrate, nonyl alcohol, nonyl acetate, nonylaldehyde, octalactone, octyl acetate, octyl alcohol, octylaldehyde, D-limonene, p-cresol, p-cresyl methyl ether, p-cymene, p-isopropyl-p-methylacetophenone, phenethyl anthranilate, phenoxyethanol, phenylacetaldehyde, phenylethyl acetate, phenylethyl alcohol, phenylethyldimethylcarbinol, α-pinene, β-pinene, α-terpinene, γ-terpinene, terpineol, terpinyl acetate, terpinyl propionate, tetrahydrolinalool, tetrahydromyrcenol, thymol, prenyl acetate, propyl butyrate, pulegone, safrole, δ-undecalactone, γ-undecalactone, undecanal, undecyl alcohol, veratrol, verdox, vertenex, viridine.

Addition of urease inhibitors to inhibit the formation or activity of enzymes responsible for the cleavage of urea into ammonia and hence for odor evolution.

Addition of antimicrobial substances. Enzymes control bacterial growth and thereby minimize odor development due to bacterial degradation processes (e.g., oxidoreductase+mediator). Examples of antimicrobial substances include quaternary ammonium compounds, phenols, amides, acids and nitro compounds and also mixtures thereof.

Examples of quaternary ammonium compounds include 2-(3-anilinovinyl)-3,4-dimethyloxazolinium iodide, alkylisoquinolium bromide, benzalkonium chloride, benzethonium chloride, cetylpyridinium chloride, chlorhexidine gluconate, chlorhexidine hydrochloride, lauryltrimethylammonium compounds, methylbenzethonium chloride, stearyltrimethylammonium chloride, 2,4,5-trichlorophenoxide and also mixtures thereof.

Examples of phenols include benzyl alcohol, p-chlorophenol, chlorocresol, chloroxylenol, cresol, o-cymen-5-ol (BIOSOL), hexachlorophene, chinokitiol, isopropylmethylphenol, parabens (with methyl, ethyl, propyl, butyl, isobutyl, isopropyl, and/or sodium methyl substituents), phenethyl alcohol, phenol, phenoxyethanol, o-phenylphenol, resorcinol, resorcinol monoacetate, sodium parabens, sodium phenolsulfonate, thioxolone, 2,4,4'-trichloro-2'-hydroxydiphenyl ether, zinc phenolsulfonate, di-tert-butylphenol, hydroquinone, BHT and also mixtures thereof.

Examples of amides include diazolidinylurea, 2,4-imidazolidinedione (HYDATOIN), 3,4,4'-trichloro-carbanilide, 3-trifluoromethyl-4,4'-dichlorocarbanilide, undecylenoic acid monoethanolamide and also mixtures thereof.

Examples of acids include benzoates, benzoic acid, citric acid, dehydroacetic acid, potassium sorbate, sodium citrates, sodium dehydroacetate, sodium salicylate, sodium salicylic acid, sorbitanic acid, undecylenoic acid, zinc undecylenate, zinc oxide, zinc phenolsulfonate, ascorbic acid, acetylsalicylic acid, salicylaldehyde, salicylic acid derivatives, adipic acid, adipic acid derivatives and also mixtures thereof.

Examples of nitro compounds include 2-bromo-2-nitro-2,3-propanediol (BRONOPOL), methyldibromoglutaronitrile and propylene glycol (MERGUARD) and also mixtures thereof.

In addition the following compounds are useful as biocides: 2,5-dimethoxytetrahydrofuran, 2,5-diethoxytetrahydrofuran, 2,5-dimethoxy-2,5-dihydrofuran, 2,5-diethoxy-2,5-dihydro-furan, succinaldehyde, glutaraldehyde, glyoxal, glyoxylic acid, hexahydrotriazine, tetrahydro-3,5-dimethyl-2H-1,3,5-thiadiazine-2-thione (Dazomet), 2,4-dichloro-benzyl alcohol, benzalkonium chloride, chlorhexidine gluconate, triclosan.

Use of microcapsules which release the active substance on contact with moisture.

Use of transition metal compounds (Cu, Ag, Zn).

As well as the classes of compounds mentioned, useful odor control compounds further include the following: peroxides, bicarbonate, triclosan, plant extracts, ethereal oils, boron compounds, poly-alpha-amino acids (polylysine), imides, polyimides, PVP-iodine, use of certain polymeric substances such as chitosan, polyglycosides, oxidizing agents, cyclophanes.

In general, however, the addition of odor inhibitors will have an adverse effect on the absorption profile of superabsorbent hydrogels. The separate installation of the odor-inhibiting or deodorizing component system and of the superabsorbent material in the hygiene article generally reduces the absorption capacity. Combinations generally exhibit a worse performance profile than the individual components as such. Moreover, the individual components may separate under mechanical stress of the kind exerted in the course of the wearing of the hygiene article for example. If, however, blends are prepared where the additives adhere to the surface of the dried superabsorbent polymers, the surface properties of the absorbent hydrogels may be changed without the intrinsic absorption properties being impaired. The result may be for example a hydrophilicization or a hydrophobicization, which primarily affects the fluid uptake rate. All these polymers, however, generally have in common that the permeability through swollen gel is unsatisfactory.

Odor control on using acidic hydrogels in hygiene articles is good. However, they exhibit a worse absorption profile than is the case with pH neutral products.

The superabsorbent hydrogels used in the hygiene sector at present are addition polymers possessing a degree of neutralization in the range from 60 to 80 mol %, based on the polymerized acid-functional monomer units. However, it was found with regard to odor control that a higher pH will generally favor bacterial growth. In the process, the urea in the urine is increasingly split by urease into carbon dioxide and urea, which leads to a further increase in the pH. This in turn reinforces bacterial growth, and enzyme activity is further increased. One consequence of the raised pH is the occurrence of soft skin, making the skin more susceptible to bacterial colonization. This results directly in skin irritation which will preclude the wearing of the hygiene article for a prolonged period.

The manufacturing process of completely acidic hydrogel forming monomers is known and has been repeatedly described in the literature. EP 205 674 A1 discloses the preparation of completely acidic addition polymers at temperatures from 0 to 100° C., and preferably from 5 to 40° C., which are adjusted by subsequent partial neutralization of the hydrogels. The addition polymers are notable for improved absorption capacity and also for lower extractables. Similarly, U.S. Pat. No. 5,145,906 and EP 530 438 B1 disclose the preparation of addition polymer gels from acrylic acid with polymers containing water-soluble hydroxyl groups in an acidic polymerization, i.e., without neutralization of the monomers, which gels are subsequently comminuted and partially or completely neutralized by means of aqueous bases and subsequently subjected to postcrossslinking. However, the processes all have in common that the polymerization of the monomer solution (as shown in EP 467 073 A1) proceeds very slowly, so that only a batch process is possible. Increasing the amount of initiator or raising the polymerization temperature has an adverse effect on the absorption profile of the hydrogels. Moreover, there are appreciable problems during the manufacturing process with the subdivision of the completely acidic polymer gel, and the neutralization which is carried out subsequently merely takes place under diffusion control, so that the polymer surface has a base excess. Hydrogels prepared by acidic polymerization generally exhibit worse absorbencies under load and also an appreciable backwetting, and this has an adverse effect on the use in the hygiene sector.

On the other hand, there are processes in existence where the monomer solution has already been subjected to a partial neutralization and whose addition polymer gels are lastly adjusted to the desired degree of neutralization following the polymerization. For instance, DE 195 29 348 reports a process wherein the monomer solution is 5–30 mol %, preferably 5–20 mol % and particularly preferably 5–10 mol % neutralized, based on the acid-functional monomers, whereupon the partially neutralized monomer batch is polymerized and subsequently the addition polymer is further neutralized until at least 50 mol % of the acid groups present therein are neutralized. This process provides addition polymers having a high retention value and a high absorbency under constant and increasing pressure and also having a low level of extractables. EP 0 583 178 B1, in contrast, proposes a process for preparing superabsorbent powders consisting of partially neutralized polyacrylic acids by a sequential, inverse suspension polymerization of two charges having different degrees of neutralization (Charge I: degree of neutralization 90–100%, Charge II: degree of neutralization 50–60%), Charge II being absorbed by the polymer of Charge I before polymerization.

None of the cited processes generates hydrogel forming addition polymers which confer all the absorption profile advantages of the optimized skin pH neutral superabsorbent on acidic addition polymers, so that a distinct odor control unit is required in each case.

It is known that hydrogels having a pH of 4.5 to 5 and hence being skin-neutral products have a higher buffering capacity for ammonia, since ammonia migrates primarily to acidic pH sites. Odor control is thus ideal when acidic hydrogels are used in hygiene articles. A disadvantage is the distinctly reduced absorption capacity of aqueous fluids with regard to hydrogels of higher pH. This disadvantage necessitates higher use levels to ensure the desired absorption performance. The trend to ever thinner constructions for hygiene articles, moreover, makes increasing demands on the water-swellable hydrophilic polymers with regard to absorbency, fluid acquisition and fluid transportation within the hygiene article, so that the sole use of addition polymers of acidic pH can be ruled out unless it possesses sufficient absorption capacity.

It is also known that hydrogels of neutral pH (pH of 6.1±0.2) have a relatively high absorption capacity. At this pH, moreover, a high swell rate is observed. However, the pH of this hydrogel is above the skin pH, so that skin irritation and sensitization may occur.

It is an object of the present invention to develop a product which combines high absorption performance and swell rate with odor-binding properties by increasing the buffering of ammonia as the main component in odor formation.

We have found that this object is achieved, surprisingly, by combining the advantages of hydrogels of acidic pH and neutral pH by using mixtures of hydrogels of acidic and "neutral" pH. It has been determined that the advantages of the mixture of the two products also distinctly exceed the properties of hydrogels having the same but homogeneous pH between the two pH extremes of 4.5 and 6.0. The fraction of neutral product comprises a high absorption capacity coupled with optimal swell rate, while the acidic sites ensure the buffering of the ammonia fraction. Because the swell rate is distinctly enhanced, the normally observed caking or poisoning of the acidic hydrogels does not take place. The admixture of neutral hydrogels lengthens the diffusion paths to the acidic sites, so that improved capillarity is ensured as a further advantage.

The present invention accordingly also provides a process for producing hydrophilic superabsorbent hydrogels, which comprises acidic and neutral hydrogels being produced in two steps and then mixed in a defined ratio. These polymer mixtures surprisingly have synergistic effects. For instance, higher AUL or CRC values can be measured on the polymer mixtures than should be expected from a purely additive calculation of the corresponding values from the percentage distributions. High CRC values coupled with good odor control are desirable for example in the case of femcare articles and mild incontinence articles for adults, since thinner articles can be manufactured as a result. In the case of big or active infants or toddlers, in contrast, high AUL values coupled with good odor control can be desirable.

The invention thus provides a polymer mixture comprising hydrogel forming polymers capable of absorbing aqueous fluids, having different pH values and each being preparable by polymerization of olefinically unsaturated carboxylic acids or derivatives thereof. Polymer mixtures are mixtures of two or more dry hydrogel forming polymers capable of absorbing aqueous fluids. These may also have a residual water content which is lower than their respective CRC. Preferably the residual moisture content is less than the intrinsic weight of the superabsorbent, more preferably less than 30% by weight residual moisture and especially less than 10% by weight residual moisture. Olefinically unsaturated carboxylic acids are preferably monoethylenically unsaturated monomers. The term "derivatives thereof" comprehends salts, esters, eg $C_1$–$C_6$-alkyl esters, anhydrides, etc, which can be hydrolyzed to the free acids. Different pH values are preferably pH values below pH 7, preferably in the range from 3.5 to 6.5 and especially in the range from 4 to 6.2. The difference between the pH values of the most far apart hydrogel forming polymers capable of absorbing aqueous fluids is 0.1 pH units or more, ie for example at least 0.2, 0.3, 0.4 pH units, preferably 0.5 pH units or more, ie for example at least 0.6, 0.7, 0.8, 0.9, 1.0, 1.1, 1.2, 1.3, 1.4 pH units, more preferably 1.5 pH units or more, ie for example at least 1.6, 1.7, 1.8, 1.9, 2.0, 2.1, 2.2, 2.3, 2.4 pH units, especially 2.5 pH units or more, ie for example at least 2.6, 2.7, 2.8, 2.9, 3.0, 3.1, 3.2, 3.3, 3.4 pH units or more.

Preferred polymer mixtures are pulverulent mixtures of 2 hydrogel forming polymers capable of absorbing aqueous fluids and having different pH values.

Further preferred polymer mixtures comprise a mixture of hydrogel forming polymers capable of absorbing aqueous fluids and having a pH of from 3 to 5 (component (i)) with hydrogel forming polymers capable of absorbing aqueous fluids and having a pH of from 5.7 to 6.5 (component (ii)).

Preference is further given to polymer mixtures having a value of 45 (g/g) or more, ie for example at least 46, 47, 48, 49 (g/g), especially 50 or more, ie for example at least 51, 52, 53, 54, 55 or more, for the sum total of CRC and AUL 0.5 psi.

Preference is additionally given to polymer mixtures wherein component (i) has a pH of from 4.0 to 4.7 and component (ii) has a pH of from 5.9 to 6.1 or wherein component (i) has a pH of from 3.1 to 3.7 and component (ii) has a pH of from 5.9 to 6.1.

Preference is likewise given to polymer mixtures comprising from 0.5% by weight to 50% by weight of component (i) and from 99.5% by weight to 50% by weight of component (ii) and especially to those comprising from 90% by weight to 70% by weight, ie for example 89, 88, 87, 86, 85, 84, 83, 82, 81, 80, 79, 78, 77, 76, 75, 74, 73, 72, 71 or in between, weight % ages of component (ii). The further component or components then add up to 100% by weight in each case.

In the polymer mixtures mentioned, the components of the mixture are made of particles of the same or different size fractions, depending on application.

The individual components can be mixed before, after or during the optional surface postcrosslinking.

Also disclosed are various applications for the polymer mixtures as absorbents for aqueous fluids, dispersions and emulsions, especially various hygiene article constructions containing the above polymer mixtures.

Experimental Part

Methods of Making:

The individual water-swellable hydrophilic polymers of different pH's according to the invention are generally prepared by free radical polymerization in an aqueous solution which contains the monomers with or without grafting base and crosslinker.

a) Monomers Used

Hydrogel forming polymers are in particular polymers of (co)polymerized hydrophilic monomers, graft (co)polymers of one or more hydrophilic monomers on a suitable grafting base, crosslinked cellulose or starch ethers, crosslinked carboxymethylcellulose, partially crosslinked polyalkylene oxide or natural products that swell in aqueous fluids, for example guar derivatives, alginates and carrageenans.

Suitable grafting bases can be of natural or synthetic origin. Examples are starch, cellulose or cellulose derivatives and also other polysaccharides and oligosaccharides, polyvinyl alcohol, polyalkylene oxides, especially polyethylene oxides and polypropylene oxides, polyamines, polyamides and also hydrophilic polyesters. Suitable polyalkylene oxides have for example the formula

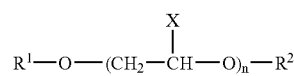

where
$R^1$ and $R^2$ are independently hydrogen, alkyl, alkenyl or aryl,

X is hydrogen or methyl and n is an integer from 1 to 10 000.

$R^1$ and $R^2$ are each preferably hydrogen, $(C_1–C_4)$-alkyl, $(C_2–C_6)$-alkenyl or phenyl.

Preferred hydrogel forming polymers are crosslinked polymers having acid groups which are predominantly in the form of their salts, generally alkali metal or ammonium salts. Such polymers swell particularly strongly on contact with aqueous fluids to form gels.

Preference is given to polymers which are obtained by crosslinking polymerization or copolymerization of acid-functional monoethylenically unsaturated monomers or derivatives thereof eg salts, esters, anhydrides. It is further possible to (co)polymerize these monomers without crosslinker and to crosslink them subsequently.

Examples of such monomers bearing acid groups are monoethylenically unsaturated $C_3$- to $C_{25}$-carboxylic acids or anhydrides such as acrylic acid, methacrylic acid, ethacrylic acid, α-chloroacrylic acid, crotonic acid, maleic acid, maleic anhydride, itaconic acid, citraconic acid, mesaconic acid, glutaconic acid, aconitic acid and fumaric acid. It is also possible to use monoethylenically unsaturated sulfonic or phosphonic acids, for example vinylsulfonic acid, allylsulfonic acid, sulfoethyl acrylate, sulfo methacrylate, sulfopropyl acrylate, sulfopropyl methacrylate, 2-hydroxy-3-acryloyloxy-propylsulfonic acid, 2-hydroxy-3-methacryloyloxypropylsulfonic acid, vinylphosphonic acid, allylphosphonic acid, styrene-sulfonic acid and 2-acrylamido-2-methylpropanesulfonic acid. The monomers may be used alone or mixed.

Preferred monomers used are acrylic acid, methacrylic acid, vinylsulfonic acid, acrylamidopropanesulfonic acid or mixtures thereof, for example mixtures of acrylic acid and methacrylic acid, mixtures of acrylic acid and acrylamidopropanesulfonic acid or mixtures of acrylic acid and vinylsulfonic acid.

To optimize properties, it can be sensible to use additional monoethylenically unsaturated compounds which do not bear an acid group but are copolymerizable with the monomers bearing acid groups. Such compounds include for example the amides and nitriles of monoethylenically unsaturated carboxylic acid, for example acrylamide, methacrylamide and N-vinylformamide, N-vinylacetamide, N-methyl-N-vinylacetamide, acrylonitrile and methacrylonitrile. Examples of further suitable compounds are vinyl esters of saturated $C_1$- to $C_4$-carboxylic acids such as vinyl formate, vinyl acetate or vinyl propionate, alkyl vinyl ethers having at least 2 carbon atoms in the alkyl group, for example ethyl vinyl ether or butyl vinyl ether, esters of monoethylenically unsaturated $C_3$- to $C_6$-carboxylic acids, for example esters of monohydric $C_1$- to $C_{18}$-alcohols and acrylic acid, methacrylic acid or maleic acid, monoesters of maleic acid, for example methyl hydrogen maleate, N-vinyllactams such as N-vinylpyrrolidone or N-vinylcaprolactam, acrylic and methacrylic esters of alkoxylated monohydric saturated alcohols, for example of alcohols having from 10 to 25 carbon atoms which have been reacted with from 2 to 200 mol of ethylene oxide and/or propylene oxide per mole of alcohol, and also monoacrylic esters and monomethacrylic esters of polyethylene glycol or polypropylene glycol, the molar masses $(M_n)$ of the polyalkylene glycols being up to 2 000, for example. Further suitable monomers are styrene and alkyl-substituted styrenes such as ethylstyrene or tert-butylstyrene.

These monomers without acid groups may also be used in mixture with other monomers, for example mixtures of vinyl acetate and 2-hydroxyethyl acrylate in any proportion. These monomers without acid groups are added to the reaction mixture in amounts within the range from 0 to 50% by weight, preferably less than 20% by weight.

Preference is given to crosslinked polymers of monoethylenically unsaturated monomers which bear acid groups and which are optionally converted into their alkali metal or ammonium salts before or after polymerization and of 0–40% by weight, based on their total weight, of monoethylenically unsaturated monomers which do not bear acid groups.

Preference is given to crosslinked polymers of monoethylenically unsaturated $C_3$- to $C_{12}$-carboxylic acids and/or their alkali metal or ammonium salts. Preference is given in particular to crosslinked polyacrylic acids where 5–30 mol %, preferably 5–20 mol % and particularly preferably 5–10 mol % of their acid groups, based on the monomers containing acid groups, are present as alkali metal or ammonium salts.

Possible crosslinkers include compounds containing at least two ethylenically unsaturated double bonds. Examples of compounds of this type are N,N'-methylenebisacrylamide, polyethylene glycol diacrylates and polyethylene glycol dimethacrylates each derived from polyethylene glycols having a molecular weight of from 106 to 8 500, preferably from 400 to 2 000, trimethylolpropane triacrylate, ethoxylated trimethylolpropane triacrylate (ETMPTA), especially ETMPTA ethoxylated with 15 EO on average, trimethylolpropane trimethacrylate, ethylene glycol diacrylate, ethylene glycol dimethacrylate, propylene glycol diacrylate, propylene glycol dimethacrylate, butanediol diacrylate, butanediol dimethacrylate, hexanediol diacrylate, hexanediol dimethacrylate, allyl methacrylate, diacrylates and dimethacrylates of block copolymers of ethylene oxide and propylene oxide, polyhydric alcohols, such as glycerol or pentaerythritol, doubly or more highly esterified with acrylic acid or methacrylic acid, triallylamine, dialkyldiallylammonium halides such as dimethyldiallylammonium chloride and diethyldiallylammonium chloride, tetraallylethylenediamine, divinylbenzene, diallyl phthalate, polyethylene glycol divinyl ethers of polyethylene glycols having a molecular weight of from 106 to 4 000, trimethylolpropane diallyl ether, butanediol divinyl ether, pentaerythritol triallyl ether, reaction products of 1 mol of ethylene glycol diglycidyl ether or polyethylene glycol diglycidyl ether with 2 mol of pentaerythritol triallyl ether or allyl alcohol, and/or divinylethyleneurea. Preference is given to using water-soluble crosslinkers, for example N,N'-methylenebisacrylamide, polyethylene glycol diacrylates and polyethylene glycol dimethacrylates derived from addition products of from 2 to 400 mol of ethylene oxide with 1 mol of a diol or polyol, vinyl ethers of addition products of from 2 to 400 mol of ethylene oxide with 1 mol of a diol or polyol, ethylene glycol diacrylate, ethylene glycol dimethacrylate or triacrylates and trimethacrylates of addition products of from 6 to 20 mol of ethylene oxide with 1 mol of glycerol, pentaerythritol triallyl ether and/or divinylurea.

Possible crosslinkers also include compounds containing at least one polymerizable ethylenically unsaturated group and at least one further functional group. The functional group of these crosslinkers has to be capable of reacting with the functional groups, essentially the acid groups, of the monomers. Suitable functional groups include for example hydroxyl, amino, epoxy and aziridino groups. Useful are for example hydroxyalkyl esters of the abovementioned monoethylenically unsaturated carboxylic acids, e.g., 2-hydroxyethyl acrylate, hydroxypropyl acrylate, hydroxybutyl acrylate, hydroxyethyl methacrylate, hydroxypropyl methacrylate and hydroxybutyl methacrylate, allylpiperidinium bromide, N-vinylimidazoles, for example N-vinylimidazole, 1-vinyl-2-methylimidazole and N-vinylimidazolines such as N-vinylimidazoline, 1-vinyl-2-methylimidazoline, 1-vinyl-2-ethylimidazoline or 1-vinyl-2-propylimidazoline, which can be used in the form of the free bases, in quaternized form or as salt in the polymerization. It is also possible to use dialkylaminoethyl acrylate and dimethylaminoethyl methacrylate, diethylaminoethyl acrylate and diethylaminoethyl methacrylate. The basic esters are preferably used in quaternized form or as salt. It is also possible to use glycidyl (meth)acrylate, for example.

Useful crosslinkers further include compounds containing at least two functional groups capable of reacting with the functional groups, essentially the acid groups, of the monomers. Suitable functional groups were already mentioned above, i.e., hydroxyl, amino, epoxy, isocyanato, ester, amido and aziridino groups. Examples of such crosslinkers are ethylene glycol, diethylene glycol, triethylene glycol, tetraethylene glycol, polyethylene glycol, glycerol, polyglycerol, triethanolamine, propylene glycol, polypropylene glycol, block copolymers of ethylene oxide and propylene oxide, ethanolamine, sorbitan fatty acid esters, ethoxylated sorbitan fatty acid esters, trimethylolpropane, pentaerythritol, 1,3-butanediol, 1,4-butanediol, polyvinyl alcohol, sorbitol, starch, polyglycidyl ethers such as ethylene glycol diglycidyl ether, polyethylene glycol diglycidyl ether, glycerol diglycidyl ether, glycerol polyglycidyl ether, diglycerol polyglycidyl ether, polyglycerol polyglycidyl ether, sorbitol polyglycidyl ether, pentaerythritol polyglycidyl ether, propylene glycol diglycidyl ether and polypropylene glycol diglycidyl ether, polyaziridine compounds such as 2,2-bishydroxymethylbutanol tris[3-(1-aziridinyl)propionate], 1,6-hexamethylenediethyleneurea, diphenylmethanebis-4,4'-N,N'-diethyleneurea, haloepoxy compounds such as epichlorohydrin and α-methylepifluorohydrin, polyisocyanates such as 2,4-toluylene diisocyanate and hexamethylene diisocyanate, alkylene carbonates such as 1,3-dioxolan-2-one and 4-methyl-1,3-dioxolan-2-one, also bisoxazolines and oxazolidones, polyamidoamines and also their reaction products with epichlorohydrin, also polyquaternary amines such as condensation products of dimethylamine with epichlorohydrin, homo- and copolymers of diallyldimethylammonium chloride and also homo- and copolymers of dimethylaminoethyl (meth)acrylate which are optionally quaternized with, for example, methyl chloride.

Useful crosslinkers further include multivalent metal ions capable of forming ionic crosslinks. Examples of such crosslinkers are magnesium, calcium, barium and aluminum ions. These crosslinkers are used for example as hydroxides, carbonates or bicarbonates. Useful crosslinkers further include multifunctional bases likewise capable of forming ionic crosslinks, for example polyamines or their quaternized salts. Examples of polyamines are ethylenediamine, diethylenetriamine, triethylenetetramine, tetraethylenepentamine, pentaethylenehexamine and polyethyleneimines and also polyamines having molar masses in each case of up to 4 000 000.

The crosslinkers are present in the reaction mixture for example from 0.001 to 20% and preferably from 0.01 to 14% by weight.

b) Free Radical Polymerization

The polymerization is initiated in the generally customary manner, by means of an initiator. But the polymerization may also be initiated by electron beams acting on the polymerizable aqueous mixture. However, the polymerization may also be initiated in the absence of initiators of the abovementioned kind, by the action of high energy radiation in the presence of photoinitiators. Useful polymerization initiators include all compounds which decompose into free radicals under the polymerization conditions, for example peroxides, hydroperoxides, hydrogen peroxides, persulfates, azo compounds and redox catalysts. The use of water-soluble initiators is preferred. In some cases it is advantageous to use mixtures of different polymerization initiators, for example mixtures of hydrogen peroxide and sodium peroxodisulfate or potassium peroxodisulfate. Mixtures of hydrogen peroxide and sodium peroxodisulfate may be used in any proportion. Examples of suitable organic peroxides are acetylacetone peroxide, methyl ethyl ketone peroxide, tert-butyl hydroperoxide, cumene hydroperoxide, tert-amyl perpivalate, tert-butyl perpivalate, tert-butyl perneohexanoate, tert-butyl perisobutyrate, tert-butyl per-2-ethylhexanoate, tert-butyl perisononanoate, tert-butyl permaleate, tert-butyl perbenzoate, di(2-ethylhexyl) peroxydicarbonate, dicyclohexyl peroxydicarbonate, di(4-tert-butylcyclohexyl) peroxydicarbonate, dimyristyl peroxydicarbonate, diacetyl peroxydicarbonate, allyl peresters, cumyl peroxyneodecanoate, tert-butyl per-3,5,5-trimethylhexanoate, acetylcyclohexylsulfonyl peroxide, dilauryl peroxide, dibenzoyl peroxide and tert-amyl perneodecanoate. Particularly suitable polymerization initiators are water-soluble azo initiators, e.g., 2,2'-azobis(2-amidinopropane) dihydrochloride, 2,2'-azobis(N,N'-dimethylene)isobutyramidine dihydrochloride, 2-(carbamoylazo)isobutyronitrile, 2,2'-azobis[2-(2'-imidazolin-2-yl)propane) dihydrochloride and 4,4'-azobis(4-cyanovaleric acid). The polymerization initiators mentioned are used in customary amounts, for example in amounts of from 0.01 to 5%, preferably from 0.05 to 2.0%, by weight, based on the monomers to be polymerized.

Useful initiators also include redox catalysts. In redox catalysts, the oxidizing component is at least one of the above-specified per compounds and the reducing component is for example ascorbic acid, glucose, sorbose, ammonium or alkali metal bisulfite, sulfite, thiosulfate, hyposulfite, pyrosulfite or sulfide, or a metal salt, such as iron(II) ions or sodium hydroxymethylsulfoxylate. The reducing component in the redox catalyst is preferably ascorbic acid or sodium sulfite. Based on the amount of monomers used in the polymerization, from $3\times10^{-6}$ to 1 mol % may be used for the reducing component of the redox catalyst system and from 0.001 to 5.0 mol % for the oxidizing component of the redox catalyst, for example.

When the polymerization is initiated using high energy radiation, the initiator used is customarily a photoinitiator. Photoinitiators include for example α-splitters, H-abstracting systems or else azides. Examples of such initiators are benzophenone derivatives such as Michler's ketone, phenanthrene derivatives, fluorene derivatives, anthraquinone derivatives, thioxanthone derivatives, coumarin derivatives, benzoin ethers and derivatives thereof, azo compounds such as the abovementioned free-radical formers, substituted hexaarylbisimidazoles or acylphosphine oxides. Examples of azides are: 2-(N,N-dimethylamino)ethyl 4-azidocinnamate, 2-(N,N-dimethyl-amino) ethyl 4-azidonaphthyl ketone, 2-(N,N-dimethylamino)ethyl 4-azidobenzoate, 5-azido-1-naphthyl 2'-(N,N-dimethylamino)ethyl sulfone, N-(4-sulfonylazidophenyl)maleimide, N-acetyl-4-sulfonylazidoaniline, 4-sulfonylazidoaniline, 4-azidoaniline, 4-azidophenacyl bromide, p-azidobenzoic acid, 2,6-bis(p-azido-benzylidene)cyclohexanone and 2,6-bis(p-azidobenzylidene)-4-methylcyclohexanone. Photoinitiators, if used, are customarily used in amounts of from 0.01 to 5% of the weight of the monomers to be polymerized.

The crosslinked polymers are preferably used in partially neutralized form. The degree of neutralization is preferably in the range from 5 to 60 mol %, more preferably in the range from 10 to 40 mol %, particularly preferably in the range from 20 to 30 mol %, based on the monomers containing acid groups. Useful neutralizing agents include alkali metal bases or ammonia/amines. Preference is given to the use of aqueous sodium hydroxide solution, aqueous potassium hydroxide solution or lithium hydroxide. However, neutralization may also be effected using sodium carbonate, sodium bicarbonate, potassium carbonate or potassium bicarbonate or other carbonates or bicarbonates or ammonia. Moreover primary, secondary and tertiary amines may be used.

Alternatively, the degree of neutralization can be set before, during or after the polymerization in all apparatuses suitable for this purpose. The neutralization can be effected for example directly in a kneader used for the polymerization. The disparate degree of neutralization is responsible for the polymers having different pH values.

Industrial processes useful for making these products include all processes which are customarily used to make superabsorbers, as described for example in Chapter 3 of "Modern Superabsorbent Polymer Technology", F. L. Buchholz and A. T. Graham, Wiley-VCH, 1998.

Polymerization in aqueous solution is preferably conducted as a gel polymerization. It involves 10–70% strength by weight aqueous solutions of the monomers and optionally of a suitable grafting base being polymerized in the presence of a free-radical initiator by utilizing the Trommsdorff-Norrish effect.

The polymerization reaction may be carried out at from 0 to 150° C., preferably at from 10 to 100° C., not only at atmospheric pressure but also at superatmospheric or reduced pressure. As is customary, the polymerization may also be conducted in a protective gas atmosphere, preferably under nitrogen.

By subsequently heating the polymer gels at from 50 to 130° C., preferably at from 70 to 100° C., for several hours, the performance characteristics of the polymers can be further improved.

c) Surface Postcrosslinking

Preference is given to hydrogel forming polymers which have been surface-postcrosslinked. Surface postcrosslinking may be carried out in a conventional manner using dried, ground and classified polymer particles.

To effect surface postcrosslinking, compounds capable of reacting with the functional groups of the polymers by crosslinking are applied to the surface of the hydrogel particles, preferably in the form of an aqueous solution. The aqueous solution may contain water-miscible organic solvents. Suitable solvents are alcohols such as methanol, ethanol, i-propanol, ethylene glycol, propylene glycol or acetone.

The subsequent crosslinking reacts polymers which have been prepared by the polymerization of the abovementioned monoethylenically unsaturated acids and optionally monoethylenically unsaturated comonomers and which have a molecular weight of greater than 5 000, preferably greater than 50 000, with compounds which have at least two groups reactive toward acid groups. This reaction can take place at room temperature or else at elevated temperatures up to 220° C.

Suitable postcrosslinkers include for example:
di- or polyglycidyl compounds such as diglycidyl phosphonates or ethylene glycol diglycidyl ether, bischlorohydrin ethers of polyalkylene glycols,
alkoxysilyl compounds,
polyaziridines, aziridine compounds based on polyethers or substituted hydrocarbons, for example bis-N-aziridinomethane,
polyamines or polyamidoamines and their reaction products with epichlorohydrin,
polyols such as ethylene glycol, 1,2-propanediol, 1,4-butanediol, glycerol, methyltriglycol, polyethylene glycols having an average molecular weight $M_w$ of 200–10 000, di- and polyglycerol, pentaerythritol, sorbitol, the ethoxylates of these polyols and their esters with carboxylic acids or carbonic acid such as ethylene carbonate or propylene carbonate,
carbonic acid derivatives such as urea, thiourea, guanidine, dicyandiamide, 2-oxazolidinone and its derivatives, bisoxazoline, polyoxazolines, di- and polyisocyanates,
di- and poly-N-methylol compounds such as, for example, methylenebis(N-methylolmethacrylamide) or melamine-formaldehyde resins,
compounds having two or more blocked isocyanate groups such as, for example, trimethylhexamethylene diisocyanate blocked with 2,2,3,6-tetramethylpiperidin-4-one.

If necessary, acidic catalysts may be added, for example p-toluenesulfonic acid, phosphoric acid, boric acid or ammonium dihydrogenphosphate.

Particularly suitable postcrosslinkers are di- or polyglycidyl compounds such as ethylene glycol diglycidyl ether, the reaction products of polyamidoamines with epichlorohydrin and 2-oxazolidinone.

The crosslinker solution is preferably applied by spraying with a solution of the crosslinker in conventional reaction mixers or mixing and drying equipment such as Patterson-Kelly mixers, DRAIS turbulence mixers, Lödige mixers, screw mixers, plate mixers, fluidized bed mixers and Schugi Mix. The spraying of the crosslinker solution may be followed by a heat treatment step, preferably in a downstream dryer, at from 80 to 230° C., preferably 80–190° C., particularly preferably at from 100 to 160° C., for from 5 minutes to 6 hours, preferably from 10 minutes to 2 hours, particularly preferably from 10 minutes to 1 hour, during which not only cracking products but also solvent fractions can be removed. But the drying may also take place in the mixer itself, by heating the jacket or by blowing in a preheated carrier gas.

In a particularly preferred embodiment of the invention, the hydrophilicity of the particle surface of the hydrogel forming polymer is additionally modified by formation of complexes. The formation of complexes on the outer shell of the hydrogel particles is effected by spraying with solutions of divalent or more highly valent metal salt solutions, and the metal cations can react with the acid groups of the polymer to form complexes.

Examples of divalent or more highly valent metal cations are $Mg^{2+}$, $Ca^{2+}$, $Al^{3+}$, $Sc^{3+}$, $Ti^{4+}$, $Mn^{2+}$, $Fe^{2+/3+}$, $Co^{2+}$, $Ni^{2+}$, $Cu^{+/2+}$, $Zn^{2+}$, $Y^{3+}$, $Zr^{4+}$, $Ag^+$, $La^{3+}$, $Ce^{4+}$, $Hf^{4+}$, and $Au^{+/3+}$, preferred metal cations are $Mg^{2+}$, $Ca^{2+}$, $Al^{3+}$, $Ti^{4+}$, $Zr^{4+}$ and $La^{3+}$, and particularly preferred metal cations are $Al^{3+}$, $Ti^{4+}$ and $Zr^{4+}$. The metal cations may be used not only alone but also mixed with each other. Of the metal cations mentioned, all metal salts are suitable that possess adequate solubility in the solvent to be used. Of particular suitability are metal salts with weakly complexing anions such as for example chloride, nitrate and sulfate. Useful solvents for the metal salts include water, alcohols, DMF, DMSO and also mixtures thereof. Particular preference is given to water and water-alcohol mixtures such as for example water-methanol or water-1,2-propanediol.

The spraying of the metal salt solution onto the particles of the hydrogel forming polymer may be effected not only before but also after the surface postcrosslinking of the particles. In a particularly preferred process, the spraying of the metal salt solution takes place in the same step as the spraying with the crosslinker solution, the two solutions being sprayed separately in succession or simultaneously via two nozzles or the crosslinker and metal salt solutions may be sprayed conjointly through a single nozzle.

Optionally, the hydrogel forming polymers may be further modified by admixture of finely divided inorganic solids, for example silica, alumina, titanium dioxide and iron(II) oxide, to further augment the effects of the surface aftertreatment. Particular preference is given to the admixture of hydrophilic silica or of alumina having an average primary particle size of from 4 to 50 nm and a specific surface area of 50–450 $m^2/g$. The admixture of finely divided inorganic solids preferably takes place after the surface modification through crosslinking/complexing, but may also be carried out before or during these surface modifications.

The surface-postcrosslinked material is generally heat treated.

Heat treatment jacket temperature: 120–180° C., preferably 140–160° C., especially 150° C.; heat treatment residence time has to be conformed to the temperature, higher temperatures involving shorter residence times and longer residence times giving more pronounced postcrosslinking. Typical values are 150 to 10 minutes.

AUL and CRC can be optimalized via the postcrosslinking time.

Properties of Acidic Hydrogel Forming Polymers According to the Invention

The inventive acidic hydrogel forming polymers or polymer mixtures capable of absorbing aqueous fluids have a particle size distribution which is generally in the range from 10 μm to about 1000 μm, preferably in the range from 100 μm to about 850 μm and especially in the range from 150 μm to about 700 μm. The size windows mentioned preferably include more than 80% by weight and especially more than 90% by weight of the particles.

The inventive polymer mixtures comprise improved odor control properties as well as high ultimate absorption capacity, high gel strength and permeability and also high retention. Owing to the presence of acidic hydrogel forming polymers, the products of the invention have antimicrobial properties, thereby providing an odor control system without the need for the addition of odor inhibiting substances or odor masking materials.

In contrast to the prior art, where an added odor control unit is indispensable for the use of superabsorbent polymers in the hygiene sector, the products of the invention permit substantially less costly manufacture, since as well as there being no need for an odor control unit there is no need either for binders or other aids for binding an odor control unit to hydrogel forming polymers.

The reduction or preferably elimination of additives for odor control purposes results in no changes to the high absorption performance and no changes to the excellent absorption behavior of the polymer mixture used. This in turn provides longer wear times when the products of the invention are used in a hygiene article. Skin sensitization and irritation is completely avoided and eliminated by a constant pH medium.

The pH of the polymer mixtures according to the invention can be measured by the methods indicated in the description part and is 6.0 or less, especially 5.9, 5.8, 5.7, 5.6, 5.5 or 5.4 and less, preferably 5.3 especially 5.2, 5.1, 5.0, 4.9 and less.

The SFC value (in $10^{-9} cm^3 s/g$) of the polymer mixture according to the invention can be measured by the methods indicated in the description part and is preferably above 1, especially 2, 4, 6, 8, 10, 12, 14, 16, 18, 20 or higher.

The CRC value [g/g] of the polymer mixture according to the invention can be measured by the methods indicated in the description part and is preferably above 15, especially 16, 18, 20, 22, 24, or higher, particularly preferably 25, especially 26, 27, 28, 29, 30, 31, 32, 33 or higher.

The AUL-0.7 psi value [g/g] of the polymer mixtures according to the invention can be measured by the methods indicated in the description part and is preferably above 4, especially 6, 8, 10, 12, or higher, particularly preferably 13, especially 14, 15, 16, 17, 18, 19, 20, 21, 22, 23, 24, 25, 26, 27, 28, or higher.

The AUL-0.5 psi value [g/g] of the polymer mixtures according to the invention can be measured by the methods indicated in the description part and is preferably above 4, especially 6, 8, 10, 12, or higher, particularly preferably 13, especially 14, 15, 16, 17, 18, 19, 20, 21, 22, 23, 24, 25, 26, 27, 28, or higher.

The Nessler value (measured as $N_2$ from $NH_3$ in mg/l compared with comparative example 1) of the hydrogel forming polymers according to the invention can be measured and calculated by the methods indicated in the description part and is at most 65% or less, especially 60%, 55%, 50% of the value of comparative example 1 or less, preferably less than 45%, especially 40%, 39%, 38%, 37%, 36%, 35%, 34%, 33%, 32%, 31%, 30%, 29%, 28%, 27%, 26%, 25%, 24%, 23%, 22%, 21%, 20% or less.

Particular preference is given to a combination of the threshold values of sum total parameters (CRC+AUL-0.5 psi) with pH or AUL-0.7 psi.

The hydrogel forming polymers capable of absorbing aqueous fluids preferably have SFC, CRC, AUL-0.7 psi and AUL-0.5 psi values as reported above for the polymer mixtures of the invention.

Deployment and Use of the Polymer Mixture

The present invention further provides for the use of the abovementioned polymer mixtures in hygiene articles comprising (A) a liquid pervious topsheet (B) a liquid impervious backsheet (C) a core positioned between (A) and (B) and comprising
10–100% by weight of the polymer mixture according to the invention
0–90% by weight of hydrophilic fiber material
preferably 20–100% by weight of the polymer mixture according to the invention, 0–80% by weight of the hydrophilic fiber material
more preferably 30–100% by weight of the polymer mixture according to the invention, 0–70% by weight of the hydrophilic fiber material
even more preferably 40–100% by weight of the polymer mixture according to the invention, 0–60% by weight of the hydrophilic fiber material much more preferably 50–100% by weight of the polymer mixture according to the invention, 0–50% by weight of the hydrophilic fiber material particularly preferably 60–100% by weight of the polymer mixture according to the invention, 0–40% by weight of the hydrophilic fiber material especially preferably 70–100% by weight of the polymer mixture according to the invention, 0–30% by weight of the hydrophilic fiber material extremely preferably 80–100% by weight of the polymer mixture according to the invention, 0–20% by weight of the hydrophilic fiber material most preferably 90–100% by weight of the polymer mixture according to the invention, 0–10% by weight of the hydrophilic fiber material (D) optionally a tissue layer positioned directly above and below said core (C) and (E) optionally an acquisition layer positioned between (A) and (C).

The preferred percentages are to be understood so that in the case of 10–100% by weight 11, 12, 13, 14, 15, 16, 17, 18, 19 up to in each case 100% by weight of polymer mixture according to the invention and all in between % ages (for example 12.2%) are possible and correspondingly hydrophilic fiber material from 0 to respectively 89, 88, 87, 86, 85, 83, 82, 81% by weight and in between percentages (for example 87.8%) are possible. If further materials are present in the core, the percentages of polymer and fiber decrease accordingly. The same applies to the preferred ranges, for example in the case of extremely preferably 81, 82, 83, 84, 85, 86, 87, 88, 89% by weight can be present for the polymer mixture according to the invention and correspondingly 19, 18, 17, 16, 15, 14, 13, 12, 11% by weight of the fiber material. So the preferred range contains 20, 21, 22, 23, 24, 25, 26, 27, 28, 29 to 100% by weight of the polymer mixture according to the invention, the more preferred range 30, 31, 32, 33, 34, 35, 36, 37, 38, 39 to 100% by weight of the polymer mixture according to the invention, the even more preferred range 40, 41, 42, 43, 44, 45, 46, 47, 48, 49 to 100% by weight of polymer mixture according to the invention, the much more preferred range 50, 51, 52, 53, 54, 55, 56, 57, 58, 59 to 100% by weight of polymer mixture according to the invention, the particularly preferred range 60, 61, 62, 63, 64, 65, 66, 67, 68, 69 to 100% by weight of polymer mixture according to the invention, the especially preferred range 70, 71, 71, 72, 73, 74, 75, 76, 77, 78, 79 to 100% by weight of polymer mixture according to the invention and the most preferred range 90, 91, 92, 93, 94, 95, 96, 97, 98, 99 or 100% by weight of polymer mixture according to the invention.

Hygiene articles for the purposes of the present invention include not only incontinence pads and incontinence briefs for adults but also diapers for infants.

The liquid pervious topsheet (A) is the layer which is in direct contact with the skin of the wearer. Its material comprises customary synthetic or manufactured fibers or films of polyesters, polyolefins, rayon or natural fibers such as cotton. In the case of non-woven materials the fibers are generally joined together by binders such as polyacrylates. Preferred materials are polyesters, rayon or blends thereof, polyethylene and polypropylene. Examples of liquid pervious layers are described in WO 99/57355 A1, EP 102 388 3 A2.

The liquid impervious layer (B) is generally a sheet of polyethylene or polypropylene.

The core (C) includes not only the polymer mixture of the invention but also hydrophilic fiber material. By hydrophilic is meant that aqueous fluids spread quickly over the fiber. The fiber material is usually a cellulose, modified cellulose, rayon, polyester such as polyethylene terephthlate. Particular preference is given to cellulose fibers such as pulp. The fibers generally have a diameter of 1–200 µm, and preferably 10–100 µm, and also have a minimum length of 1 mm.

Diaper construction and shape is common knowledge and described for example in WO 95/26209 page 66 line 34 to page 69 line 11, DE 196 04 601 A1, EP-A-0 316 518 and EP-A-0 202 127. Diapers and other hygiene articles are generally also described in WO 00/65084, especially at pages 6–15, WO 00/65348, especially at pages 4–17, WO 00/35502, especially pages 3–9, DE 19737434, WO 98/8439. Hygiene articles for feminine hygiene are described in the following references. The inventive polymer mixtures capable of absorbing aqueous fluids can be used there. Femcare references: WO 95/24173: Absorption Article for Controlling Odour, WO 91/11977: Body Fluid Odour Control, EP 389023: Absorbent Sanitary Articles, WO 94/25077: Odour Control Material, WO 97/01317: Absorbent Hygienic Article, WO 99/18905, EP 834297, U.S. Pat. No. 5,762,644, U.S. Pat. No. 5,895,381, WO 98/57609, WO 2000/065083, WO 2000/069485, WO 2000/069484, WO 2000/069481, U.S. Pat. No. 6,123,693, EP 1104666, WO 2001/024755, WO 2001/000115, EP 105373, WO 2001/041692, EP 1074233. Tampons are described in the following references: WO 98/48753, WO 98/41179, WO 97/09022, WO 98/46182, WO 98/46181, WO 2001/043679, WO 2001/043680, WO 2000/061052, EP 1108408, WO 2001/033962, DE 200020662, WO 2001/001910, WO 2001/001908, WO 2001/001909, WO 2001/001906, WO 2001/001905, WO 2001/24729. Incontence articles are described in the following references: Disposable Absorbent Article for Incontinent Individuals: EP 311344 description pages 3–9; Disposable Absorbent Article: EP 850623; Absorbent Article: WO 95/26207; Absorbent Article: EP 894502; Dry Laid Fibrous Structure: EP 850 616; WO 98/22063; WO 97/49365; EP 903134; EP 887060; EP 887059; EP 887058; EP 887057; EP 887056; EP 931530; WO 99/25284; WO 98/48753. Femcare and incontinence articles are described in the following references: Catamenial Device: WO 93/22998 description pages 26–33; Absorbent Members for Body Fluids: WO 95/26209 description pages 36–69; Disposable Absorbent Article: WO 98/20916 description pages 13–24; Improved Composite Absorbent Structures: EP 306262 description pages 3–14; Body Waste Absorbent Article: WO 99/45973. These references and the references therein are hereby expressly incorporated in the disclosure of the present invention.

The polymer mixtures according to the invention are very useful as absorbents for water and aqueous fluids, so that they may be used with advantage as a water retainer in market gardening, as a filter aid and particularly as an absorbent component in hygiene articles such as diapers, tampons or sanitary napkins.

Incorporation and Fixation of the Highly Swellable Hydrogels According to the Invention In addition to the above-described highly swellable hydrogels (polymer mixture), the absorbent composition of the present invention includes constructions which include highly swellable hydrogels or to which they are fixed. Any construction is suitable that is capable of accommodating highly swellable hydrogels and of being integrated into the absorption layer. A multiplicity of such compositions is already known and described in detail in the literature. A construction for installing the highly swellable hydrogels can be for example a fiber matrix consisting of a cellulose fiber mixture (air-laid web, wet laid web) or synthetic polymer fibers (meltblown web, spunbonded web) or else of a fiber blend of cellulose fibers and synthetic fibers. Possible fiber materials are detailed in the chapter which follows. The air-laid web process is described for example in WO 98/28 478. Furthermore, open-celled foams or the like may be used to install highly swellable hydrogels.

Alternatively, such a construction can be the result of fusing two individual layers to form one or better a multiplicity of chambers which contain the highly swellable hydrogels. Such a chamber system is described in detail in EP 0 615 736 A1 page 7 lines 26 et seq.

In this case, at least one of the two layers should be water pervious. The second layer may either be water pervious or water impervious. The layer material used may be tissues or other fabric, closed or open-celled foams, perforated films, elastomers or fabrics composed of fiber material. When the absorbent composition consists of a construction of layers, the layer material should have a pore structure whose pore dimensions are small enough to retain the highly swellable hydrogel particles. The above examples on the construction of the absorbent composition also include laminates composed of at least two layers between which the highly swellable hydrogels are installed and fixed.

Generally it is possible to fix hydrogel particles within the absorbent core to improve dry and wet integrity. Dry and wet integrity describes the ability to install highly swellable hydrogels into the absorbent composition in such a way that they withstand external forces not only in the wet but also in the dry state and highly swellable polymer does not dislocate or spill out. The forces referred to are especially mechanical stresses as occur in the course of moving about while wearing the hygiene article or else the weight pressure on the hygiene article in the case of incontinence especially. As to fixation, one skilled in the art knows a multiplicity of possibilities. Examples such as fixation by heat treatment, addition of adhesives, thermoplastics, binder materials are noted in WO 95/26 209 page 37 line 36 to page 41 line 14. The cited passage is thus part of this invention. Methods for enhancing wet strength are also to be found in WO 2000/36216 A1.

Furthermore, the absorbent composition may comprise a base material, for example a polymer film on which the highly swellable hydrogel particles are fixed. The fixing may be effected not only on one side but also on both sides. The base material can be water pervious or water impervious.

The above constructions of the absorbent composition incorporate the highly swellable hydrogels at a weight fraction of from 10–100% by weight, preferably 20–100% by weight, more preferably 30–100% by weight, even more preferably 40–100% by weight, much more preferably 50–100% by weight, particularly preferably 60–100% by weight, especially preferably 70–100% by weight, extremely preferably 80–100% by weight and most preferably 90–100% by weight, based on the total weight of the construction and of the highly swellable hydrogels.

Fiber Materials of the Absorbent Composition

The structure of the present absorbent composition according to the invention may be based on various fiber materials, which are used as a fiber network or matrices. The present invention includes not only fibers of natural origin (modified or unmodified) but also synthetic fibers.

A detailed overview of examples of fibers which can be used in the present invention is given in WO 95/26 209 page 28 line 9 to page 36 line 8. The cited passage is thus part of this invention.

Examples of cellulose fibers include cellulose fibers which are customarily used in absorption products, such as fluff pulp and cellulose of the cotton type. The materials (soft- or hardwoods), production processes such as chemical pulp, semichemical pulp, chemothermo-mechanical pulp (CTMP) and bleaching processes are not particularly restricted. For instance, natural cellulose fibers such as cotton, flax, silk, wool, jute, ethylcellulose and cellulose acetate are used.

Suitable synthetic fibers are produced from polyvinyl chloride, polyvinyl fluoride, polytetrafluoroethylene, polyvinylidene chloride, polyacrylic compounds such as ORLON®, polyvinyl acetate, polyethyl vinyl acetate, soluble or insoluble polyvinyl alcohol. Examples of synthetic fibers include thermoplastic polyolefin fibers, such as polyethylene fibers (PULPEX®), polypropylene fibers and polyethylene-polypropylene bicomponent fibers, polyester fibers, such as polyethylene terephthalate fibers (DACRON® or KODEL®), copolyesters, polyvinyl acetate, polyethyl vinyl acetate, polyvinyl chloride, polyvinylidene chloride, polyacrylics, polyamides, copolyamides, polystyrene and copolymers of the aforementioned polymers and also bicomponent fibers composed of polyethylene terephthalate-polyethylene-isophthalate copolymer, polyethyl vinyl acetate/polypropylene, polyethylene/polyester, polypropylene/polyester, copolyester/polyester, polyamide fibers (nylon), polyurethane fibers, polystyrene fibers and polyacrylonitrile fibers. Preference is given to polyolefin fibers, polyester fibers and their bicomponent fibers. Preference is further given to thermally adhesive bicomponent fibers composed of polyolefin of the core-sheath type and side-by-side type on account of their excellent dimensional stability following fluid absorption.

The synthetic fibers mentioned are preferably used in combination with thermoplastic fibers. In the course of the heat treatment, the latter migrate to some extent into the matrix of the fiber material present and so constitute bond sites and renewed stiffening elements on cooling. Additionally the addition of thermoplastic fibers means that there is an increase in the present pore dimensions after the heat treatment has taken place. This makes it possible, by continuous addition of thermoplastic fibers during the formation of the absorbent core, to continuously increase the fraction of thermoplastic fibers in the direction of the topsheet, which results in a similarly continuous increase in the pore sizes. Thermoplastic fibers can be formed from a multiplicity of thermoplastic polymers which have a melting point of less than 190° C., preferably in the range from 75° C. to 175° C. These temperatures are too low for damage to the cellulose fibers to be likely.

Lengths and diameters of the above-described synthetic fibers are not particularly restricted, and generally any fiber from 1 to 200 mm in length and from 0.1 to 100 denier (gram per 9 000 meters) in diameter may preferably be used. Preferred thermoplastic fibers are from 3 to 50 mm in length, particularly preferred thermoplastic fibers are from 6 to 12 mm in length. The preferred diameter for the thermoplastic fiber is in the range from 1.4 to 10 decitex, and the range from 1.7 to 3.3 decitex (gram per 10 000 meters) is particularly preferred. The form of the fiber may vary; examples include woven types, narrow cylindrical types, cut/chopped yarn types, staple fiber types and continuous filament fiber types.

The fibers in the absorbent composition of the invention can be hydrophilic, hydrophobic or a combination thereof. According to the definition of Robert F. Gould in the 1964 American Chemical Society publication "Contact angle, wettability and adhesion", a fiber is referred to as hydrophilic when the contact angle between the liquid and the fiber (or the fiber surface) is less than 90° or when the liquid tends to spread spontaneously on the same surface. The two processes are generally coexistent. Conversely, a fiber is termed hydrophobic when a contact angle of greater than 90° is formed and no spreading is observed.

Preference is given to using hydrophilic fiber material. Particular preference is given to using fiber material which is weakly hydrophilic on the body side and most hydrophilic in the region surrounding the highly swellable hydrogels. In the manufacturing process, layers having different hydrophilicities are used to create a gradient which channels impinging fluid to the hydrogel, where it is ultimately absorbed.

Suitable hydrophilic fibers for use in the absorbent composition of the invention include for example cellulose fibers, modified cellulose fibers, rayon, polyester fibers, for example polyethylene terephthalate (DACRON®), and hydrophilic nylon (HYDROFIL®). Suitable hydrophilic fibers may also be obtained by hydrophilicizing hydrophobic fibers, for example the treatment of thermoplastic fibers obtained from polyolefins (e.g. polyethylene or polypropylene, polyamides, polystyrenes, polyurethanes, etc.) with surfactants or silica. However, for cost reasons and ease of availability, cellulosic fibers are preferred.

The highly swellable hydrogel particles are embedded into the fiber material described. This can be done in various ways, for example by using the hydrogel material and the fibers together to create an absorbent layer in the form of a matrix, or by incorporating highly swellable hydrogels into fiber mixture layers, where they are ultimately fixed, whether by means of adhesive or lamination of the layers.

The fluid-acquiring and -distributing fiber matrix may comprise synthetic fiber or cellulosic fiber or a mixture of synthetic fiber and cellulosic fiber, in which case the mixing ratio may vary from (100 to 0) synthetic fiber: (0 to 100) cellulosic fiber. The cellulosic fibers used may additionally have been chemically stiffened to increase the dimensional stability of the hygiene article.

The chemical stiffening of cellulosic fibers may be provided in different ways. A first way of providing fiber stiffening is by adding suitable coatings to the fiber material. Such additives include for example polyamide-epichlorohydrin coatings (Kymene® 557H, Hercoles, Inc. Wilmington, Del.), polyacrylamide coatings (described in U.S. Pat. No. 3,556,932 or as the Parez® 631 NC commercial product from American Cyanamid Co., Stamford, Conn.), melamine-formaldehyde coatings and polyethyleneimine coatings.

Cellulosic fibers may also be chemically stiffened by chemical reaction. For instance, suitable crosslinker substances may be added to effect crosslinking taking place within the fiber. Suitable crosslinker substances are typical substances used for crosslinking monomers including but not limited to $C_2$–$C_8$-dialdehydes, $C_2$–$C_8$-monoaldehydes having acid functionality and in particular $C_2$–$C_9$-polycarboxylic acids. Specific substances from this series are for example glutaraldehyde, glyoxal, glyoxylic acid, formaldehyde and citric acid. These substances react with at least 2 hydroxyl groups within any one cellulose chain or between two adjacent cellulose chains within any one cellulose fiber. The crosslinking causes a stiffening of the fibers, to which greater dimensional stability is imparted as a result of this treatment. In addition to their hydrophilic character, these fibers exhibit uniform combinations of stiffening and elasticity. This physical property makes it possible to retain the capillary structure even under simultaneous contact with fluid and compressive forces and to prevent premature collapse.

Chemically crosslinked cellulose fibers are known and described in WO 91/11162, U.S. Pat. No. 3,224,926, U.S. Pat. No. 3,440,135, U.S. Pat. No. 3,932,209, U.S. Pat. No. 4,035,147, U.S. Pat. No. 4,822,453, U.S. Pat. No. 4,888,093, U.S. Pat. No. 4,898,642 and U.S. Pat. No. 5,137,537. The chemical crosslinking imparts stiffening to the fiber material, which is ultimately reflected in improved dimensional stability for the hygiene article as a whole. The individual layers are joined together by methods known to one skilled in the art, for example intermelting by heat treatment, addition of hot-melt adhesives, latex binders, etc.

Methods of Making the Absorbent Composition

The absorbent composition is composed of constructions which contain acidic highly swellable hydrogels and the acidic highly swellable hydrogels which are present in said constructions or fixed thereto.

Examples of processes to obtain an absorbent composition comprising for example a base material to which highly swellable hydrogels are fixed on one or both sides are known and included by the invention but not limited thereto.

Examples of processes to obtain an absorbent composition comprising for example a fiber material blend of synthetic fibers (a) and cellulose fibers (b) embedded in highly swellable hydrogels (c), the blend ratio varying from (100 to 0) synthetic fiber: (0 to 100) cellulose fiber, include (1) a process where (a), (b) and (c) are mixed together at one and the same time, (2) a process where a mixture of (a) and (b) is mixed into (c), (3) a process where a mixture of (b) and (c) is mixed with (a), (4) a process where a mixture of (a) and (c) is mixed into (b), (5) a process where (b) and (c) are mixed and (a) is continuously metered in, (6) a process where (a) and (c) are mixed and (b) is continuously metered in, and (7) a process where (b) and (c) are mixed separately into (a). Of these examples, processes (1) and (5) are preferred. The apparatus used in this process is not particularly restricted and any customary apparatus known to one skilled in the art can be used.

The absorbent composition obtained in this way can optionally be subjected to a heat treatment, so that an absorption layer having excellent dimensional stability in the moist state is obtained. The heat treatment process is not particularly restricted. Examples include heat treatment by feeding hot air or infrared irradiation. The temperature of the heat treatment is in the range from 60° C. to 230° C., preferably from 100° C. to 200° C., particularly preferably from 100° C. to 180° C. The duration of the heat treatment depends on the type of synthetic fiber, its amount and the hygiene article production rate. Generally the duration of the heat treatment is in the range from 0.5 second to 3 minutes, preferably from 1 second to 1 minute.

The absorbent composition is generally provided for example with a liquid-pervious topsheet and a liquid-impervious backsheet. Furthermore, leg cuffs and adhesive tabs are attached to finalize the hygiene article. The materials and types of pervious topsheet and impervious backsheet and of the leg cuffs and adhesive tabs are known to one skilled in the art and are not particularly restricted. Examples thereof may be found in WO 95/26 209.

Experimental Part

Test Methods a) Centrifuge Retention Capacity (CRC)

This method measures the free swellability of the hydrogel in a teabag. 0.2000±0.0050 g of dried hydrogel (particle size fraction 106–850 µm) are weighed into a teabag 60×85 mm in size which is subsequently sealed. The teabag is placed for 30 minutes in an excess of 0.9% by weight sodium chloride solution (at least 0.83 l of sodium chloride solution/1 g of polymer powder). The teabag is then centrifuged for 3 minutes at 250 g. The amount of liquid is determined by weighing back the centrifuged teabag.

b) Absorbency Under Load (AUL) (0.7 psi)

The measuring cell for determining AUL 0.7 psi is a Plexiglass cylinder 60 mm in internal diameter and 50 mm in height. Adhesively attached to its underside is a stainless steel sieve bottom having a mesh size of 36 µm. The measuring cell further includes a plastic plate having a diameter of 59 mm and a weight which can be placed in the measuring cell together with the plastic plate. The plastic plate and the weight together weigh 1 345 g. AUL 0.7 psi is determined by determining the weight of the empty Plexiglass cylinder and of the plastic plate and recording it as $W_0$. 0.900±0.005 g of hydrogel forming polymer (particle size distribution 150–800 µm) is then weighed into the Plexiglass cylinder and distributed very uniformly over the stainless steel sieve bottom. The plastic plate is then carefully placed in the Plexiglass cylinder, the entire unit is weighed and the weight is recorded as $W_a$. The weight is then placed on the plastic plate in the Plexiglass cylinder. A ceramic filter plate 120 mm in diameter and 0 in porosity is then placed in the middle of a Petri dish 200 mm in diameter and 30 mm in height and sufficient 0.9% by weight sodium chloride solution is introduced for the surface of the liquid to be level with the filter plate surface without the surface of the filter plate being wetted. A round filter paper 90 mm in diameter and <20 µm in pore size (S&S 589 Schwarzband from Schleicher & Schüll) is subsequently placed on the ceramic plate. The Plexiglass cylinder containing hydrogel forming polymer is then placed with plastic plate and weight on top of the filter paper and left there for 60 minutes. At the end of this period, the complete unit is removed from the filter paper and the Petri dish and subsequently the weight is removed from the Plexiglass cylinder. The Plexiglass cylinder containing swollen hydrogel is weighed together with the plastic plate and the weight recorded as $W_b$.

AUL was calculated by the following equation:

$$AUL\ 0.7\ psi\ [g/g] = [W_b - W_a]/[W_a - W_0]$$

AUL-0.5 psi is measured using a correspondingly lighter weight on the plastic plate.

c) Saline Flow Conductivity (SFC)

The test method for determining SFC is described in U.S. Pat. No. 5,599,335.

d) pH Measurement of Hydrogel Forming Polymers 100 ml of 0.9% by weight NaCl solution is magnetically stirred at moderate speed in a 150 ml beaker without air being drawn into the solution. This solution is admixed with 0.5±0.001 g of hydrogel forming polymer and stirred for 10 minutes. After 10 minutes, the pH of the solution is measured with a pH glass electrode, the value not being read off until it is stable, but at the earliest after 1 minute.

e) Ammonia Determination for Odor Control

The ammonia nitrogen content is determined calorimetrically by the Nessler method. Urea eliminates ammonia under the action of urease; a yellow color develops to a degree proportional to the ammonia concentration.

5 g of the various superabsorbent samples were saturated with 600 ml of 0.9% NaCl and 1.8% urea solution for 20 min. The solutions were filtered and 25 ml of the solution were admixed with 10 µl of urease solution. After 2 minutes nitrogen from ammonia was determined by the Nessler method.

EXAMPLES

The polymer mixtures obtained in the inventive examples are distinguished from the polymers obtained in the comparative examples by a combination of absorption quantity and swell rate and exhibit a high fluid permeability and also improved odor control properties. They are therefore very useful as absorbents for water and aqueous fluids, especially body fluids, for example urine or blood, for example in hygiene articles such as for example infant and adult diapers, sanitary napkins, tampons and the like.

The examples hereinbelow illustrate the invention.

Comparative Example 1 a) In a 40 l plastic bucket, 6.9 kg of glacial acrylic acid are diluted with 20 kg of deionized water. 33 g of pentaerythritol triallyl ether are added to this solution with stirring, and the sealed bucket is inertized by passing nitrogen through it. The polymerization is then initiated by adding 0.4 g of hydrogen peroxide dissolved in 40 ml of deionized water and 0.2 g of ascorbic acid dissolved in 40 ml of deionized water. After the reaction has ended, the gel is mechanically comminuted and mixed with sufficient aqueous sodium hydroxide solution for a degree of neutralization of 75 mol %, based on acrylic acid used. The neutralized gel is then dried on a can dryer, ground with a pin mill and finally screened off at 150–850 µm.

b) The base polymer prepared under a) was sprayed with 2.9% by weight of crosslinker solution composed of 49.56 parts by weight of 1,2-propanediol, 49.56 parts by weight of deionized water and 0.88 part by weight of monoethylene glycol diglycidyl ester (EDGE) in a Lödige laboratory mixer, the percentages being based on base polymer. The moist product was then transferred into a second preheated Lödige laboratory mixer and annealed at 140° C. for 60 minutes. The dried product was cooled down to room temperature and screened off at 850 µm.

Comparative Example 2 a) In a 40 l plastic bucket, 6.9 kg of glacial acrylic acid are diluted with 20 kg of deionized water. 33 g of pentaerythritol triallyl ether are added to this solution with stirring, and the sealed bucket is inertized by passing nitrogen through it. The polymerization is then initiated by adding 0.4 g of hydrogen peroxide dissolved in 40 ml of deionized water and 0.2 g of ascorbic acid dissolved in 40 ml of deionized water. After the reaction has ended, the gel is mechanically comminuted and mixed with sufficient aqueous sodium hydroxide solution for a degree of neutralization of 75 mol %, based on acrylic acid used. The neutralized gel is then dried on a can dryer, ground with a pin mill and finally screened off at 150–850 μm.)

b) The base polymer prepared under a) was sprayed with 3.75% by weight of crosslinker solution composed of 33.3 parts by weight of 1,2-propanediol, 63.5 parts by weight of deionized water and 3.2 parts by weight of EDGE and also with 0.12 part by weight of a 27% aqueous aluminum sulfate solution in a Lödige laboratory mixer, the percentages being based on base polymer. Crosslinker solution and aluminum sulfate solution are sprayed separately but simultaneously from 2 nozzles. The moist product was then transferred into a second preheated Lödige laboratory mixer and annealed at 140° C. for 60 minutes. The dried product was cooled down to room temperature and screened off at 850 μm.

Comparative Example 3

A 10 l capacity polyethylene vessel thoroughly insulated with foamed plastic material is charged with 3928 g of completely ion-free water, 625 g of sodium bicarbonate are suspended in the water and 2000 g of acrylic acid are added with stirring so that there is no over-foaming due to ensuing $CO_2$ evolution. This is followed by the addition, in succession, of an emulsion of 1.3 g of sorbitan monococoate in 100 g of completely ion-free water and 8.1 g of allyl methacrylate, and the solution is further inertized by passing nitrogen into it. This is followed by the addition of the initiator system, consisting of 1.66 g of 2,2'-azobisamidinopropane dihydrochloride (dissolved in 20 g of completely ion-free water), 3.33 g of potassium peroxodisulfate (dissolved in 150 g of completely ion-free water) and also 0.3 g of ascorbic acid (dissolved in 25 g of completely ion-free water) in succession with stirring. The reaction solution is then left to stand without stirring. The polymerization which ensues, and in the course of which the temperature rises to about 90° C., produces a solid gel. This solid gel is mechanically comminuted using a meat grinder, dried on VA stainless steel wire mesh in a circulating air drying cabinet at 160° C., then ground and screened.

Comparative Example 4

TYLOSE VS 3790, a superabsorbent from CASSELLA AG of Frankfurt/Main, characterized by a pH of 5–5.5, prepared similarly to example 7 of EP 0 316 792 B1

Comparative Example 5

Under adiabatic conditions, a 2 l wide-neck cylindrical reaction flask is charged with 1108 g of deionized water cooled to 15° C., and 375 g of acrylic acid, and 1.8 g of pentaerythritol triallyl ether. Nitrogen is passed into the monomer solution at a rate of about 2 g/min for about 20 min to lower the oxygen content. At an $O_2$ content of 1.5 ppm, a solution of 0.18 g of 2,2'-azobis(2-amidinopropane) dihydrochloride in 4.3 g of deionized water is added, followed after passing in further $N_2$ and at an $O_2$ content of 1.3 ppm, by 0.066 g of a 34% $H_2O_2$ solution diluted with 3 g of deionized water and finally, at an $O_2$ content of 1.0 ppm, by 0.009 g of ascorbic acid dissolved in 7.4 g of deionized water. The ensuing polymerization, in the course of which the temperature rises to about 75° C., produces a solid, milkily cloudy gel, which is subsequently subjected to mechanical comminution. 1000 g of the comminuted gel are admixed with 27.8 g of 50% aqueous sodium hydroxide solution previously diluted with 72.2 g of water (degree of neutralization of the acrylic acid 10 mol %), and passed twice through a mixing extruder, and the resultant gel particles are dried at 50° C. under reduced pressure, then ground and screened.

Inventive Example 1

5 parts of powder from comparative example 3 and 95 parts from comparative example 2 are mixed in a laboratory tumble mixer for 60 minutes until homogeneous.

Inventive Example 2

10 parts of powder from comparative example 3 and 90 parts from comparative example 2 are mixed in a laboratory tumble mixer for 60 minutes until homogeneous.

Inventive Example 3

20 parts of powder from comparative example 3 and 80 parts from comparative example 2 are mixed in a laboratory tumble mixer for 60 minutes until homogeneous.

Inventive Example 4

30 parts of powder from comparative example 3 and 70 parts from comparative example 2 are mixed in a laboratory tumble mixer for 60 minutes until homogeneous.

Inventive Example 5

10 parts of powder from comparative example 5 and 90 parts from comparative example 1 are mixed in a laboratory tumble mixer for 60 minutes until homogeneous.

Inventive Example 6

20 parts of powder from comparative example 5 and 80 parts from comparative example 1 are mixed in a laboratory tumble mixer for 60 minutes until homogeneous.

Inventive Example 7

30 parts of powder from comparative example 5 and 70 parts from comparative example 1 are mixed in a laboratory tumble mixer for 60 minutes until homogeneous.

Inventive Example 8

40 parts of powder from comparative example 5 and 60 parts from comparative example 1 are mixed in a laboratory tumble mixer for 60 minutes until homogeneous.

The performance data of inventive examples 1 to 4 are revealed in table 1 and those of inventive examples 5 to 8 in table 2.

TABLE 1

| Example | Mixing ratio | | CRC g/g | AUL 0.5 psi g/g | AUL 0.7 psi g/g | SFC | pH |
| --- | --- | --- | --- | --- | --- | --- | --- |
| | Comparative 2 % by weight | Comparative 1 % by weight | | | | | |
| Comparative 2 | 100 | — | 29 | 26 | 23 | 15 | 6.1 |
| Inventive 1 | 95 | 5 | 27 | 26 | 23 | 15 | 6.0 |
| Inventive 2 | 90 | 10 | 27 | 25 | 23 | 14 | 5.9 |
| Inventive 3 | 80 | 20 | 27 | 25 | 22 | 11 | 5.7 |
| Inventive 4 | 70 | 30 | 27 | 24 | 21 | 10 | 5.4 |
| Comparative 3 | — | 100 | 23 | 11 | 7 | 3 | 4.5 |
| Comparative 4 | — | 100 | 42 | 12 | 6.0 | ≦1 | 5.4 |

Comparative example 4 is the control for inventive example 4 and shows that a product of the same pH has a high CRC but also a distinctly lower absorbency under load and virtually no permeability. The overall performance is thus distinctly worse and the use in thinner diapers can thus be ruled out.

TABLE 2

| Example | Mixing ratio | | CRC g/g | AUL 0.5 psi g/g | AUL 0.7 psi g/g | SFC | pH |
| --- | --- | --- | --- | --- | --- | --- | --- |
| | Comparative 1 % by weight | Comparative 3 % by weight | | | | | |
| Comparative 1 | 100 | — | 33.4 | 29.4 | 22.8 | 5 | 5.95 |
| Inventive 5 | 90 | 10 | 33.1 | 26.7 | 19.6 | 4 | 5.64 |
| Inventive 6 | 80 | 20 | 32.5 | 23.9 | 18.3 | 4 | 5.38 |
| Inventive 7 | 70 | 30 | 31.2 | 19.7 | 14.6 | 2 | 5.10 |
| Inventive 8 | 60 | 40 | 30.1 | 17.8 | 12.9 | 2 | 4.93 |
| Comparative 5 | — | 100 | 10.9 | 7.0 | 5.1 | 1 | 3.39 |

We claim:

1. A polymer mixture comprising hydrogel forming polymers having different pH values below pH 7 and each prepared by polymerization of olefinically unsaturated carboxylic acids or a salt, ester, or anhydride thereof.

2. The polymer mixture as claimed in claim 1, being pulverulent mixtures of two hydrogel forming polymers having different pH values.

3. The polymer mixture as claimed in claim 1 comprising a mixture of hydrogel forming polymers having a pH of from 3 to 5 (component (i)) with hydrogel forming polymers having a pH of from 5.7 to 6.5 (component (ii)).

4. The polymer mixture as claimed in claim 1 having a value of at least 45 (g/g) for the sum total of CRC and AUL 0.5 psi.

5. The polymer mixture as claimed in claim 3 wherein component (i) has a pH of from 4.0 to 4.7 and component (ii) has a pH of from 5.9 to 6.1.

6. The polymer mixture as claimed in claim 3 comprising from 0.5% by weight to 50% by weight of component (i) and from 99.5% by weight to 50% by weight of component (ii).

7. The polymer mixture as claimed in claim 3 wherein component (ii) is present in an amount ranging from 90% by weight to 70% by weight.

8. The polymer mixture as claimed in claim 1 wherein the components of the mixture are prepared from particles of the same size fraction.

9. The polymer mixture as claimed in claim 1 wherein the components of the mixture are prepared from particles of different size fractions.

10. A hygiene article comprising a polymer mixture as claimed in claim 1.

11. A method of absorbing an aqueous fluid, dispersion, or emulsion comprising the step of contacting the fluid, dispersion, or emulsion with a polymer mixture of claim 1.

* * * * *

UNITED STATES PATENT AND TRADEMARK OFFICE
CERTIFICATE OF CORRECTION

PATENT NO. : 7,144,957 B2 Page 1 of 1
APPLICATION NO. : 10/490403
DATED : December 5, 2006
INVENTOR(S) : Rüdiger Funk et al.

It is certified that error appears in the above-identified patent and that said Letters Patent is hereby corrected as shown below:

Title Page, Item (54): Title and Column 1, Lines 1–2,
Please delete:
"POLYMER MIXTURE OF HYDROGELS WITH DIFFERENT PH VALUE"

and insert
-- HIGHLY SWELLABLE HYDROGELS WITH ACIDIC CENTERS --
in its place.

Signed and Sealed this

Twenty-fourth Day of April, 2007

JON W. DUDAS
*Director of the United States Patent and Trademark Office*